United States Patent [19]
Cooke et al.

[11] Patent Number: 5,852,058
[45] Date of Patent: Dec. 22, 1998

[54] INTRAMURAL DELIVERY OF NITRIC OXIDE ENHANCER FOR INHIBITING LESION FORMATION AFTER VASCULAR INJURY

[75] Inventors: John P. Cooke, Palo Alto; Sverin Schwarzacher, Menlo Park, both of Calif.; Tai T. Lim, Gillman Heights, Singapore; Alan C. Yeung, Hillsborough, Calif.

[73] Assignee: The Board of Trustees of the Leland Stanford Junior University, Palo Alto, Calif.

[21] Appl. No.: 695,792

[22] Filed: Aug. 12, 1996

Related U.S. Application Data

[63] Continuation-in-part of Ser. No. 556,035, Nov. 9, 1995, which is a continuation-in-part of Ser. No. 336,159, Nov. 8, 1994, abandoned, which is a continuation-in-part of Ser. No. 076,312, Jun. 11, 1993, Pat. No. 5,428,070.

[51] Int. Cl.$^6$ .................... A61K 31/195; A61K 38/02; A61M 25/10; A61N 1/30
[52] U.S. Cl. ................. 514/564; 514/2; 514/565; 604/21; 604/53
[58] Field of Search .................. 514/2, 20, 564, 514/565; 204/550; 424/424; 604/20, 21, 53, 96, 97, 98, 272, 280; 607/3

[56] References Cited

U.S. PATENT DOCUMENTS

| | | | |
|---|---|---|---|
| 5,171,217 | 12/1992 | March et al. | 604/53 |
| 5,236,413 | 8/1993 | Feiring | 604/21 |
| 5,286,254 | 2/1994 | Shapland et al. | 604/21 |
| 5,318,531 | 6/1994 | Leone | 604/96 |
| 5,428,070 | 6/1995 | Cooke et al. | 514/557 |
| 5,482,925 | 1/1996 | Hutsell | 514/11 |
| 5,499,971 | 3/1996 | Shapland et al. | 604/53 |
| 5,569,198 | 10/1996 | Racchini | 604/96 |
| 5,628,730 | 5/1997 | Shapland et al. | 604/21 |
| 5,634,895 | 6/1997 | Igo et al. | 604/21 |

OTHER PUBLICATIONS

McNamara et al., L–Arginine Inhibits Balloon Catheter... Biochem, Biophys. Res. Comm. vol. 193, No. 1, pp. 291–296 May 28, 1993.

*Primary Examiner*—Jeffrey E. Russel
*Attorney, Agent, or Firm*—Bertram I. Rowland

[57] ABSTRACT

Vessels suffering vascular injury from angioplasty are treated with L-arginine intramurally. The incidents associated with restenosis are substantially reduced providing for a reduced incidence of restenosis as a result of the injury.

7 Claims, 10 Drawing Sheets

BEFORE — FIG. 3A

AFTER — FIG. 3B

LOCAL DRUG DELIVERY

INTRAMURAL DELIVERY OF NITRIC OXIDE ENHANCER FOR INHIBITING LESION FORMATION AFTER VASCULAR INJURY

CROSS-REFERENCE TO RELATED APPLICATIONS

This application is a continuation-in-part of application Ser. No. 08/556,035, filed Nov. 9, 1995, which is a continuation-in-part of application Ser. No. 08/336,159, filed Nov. 8, 1994, now abandoned, which is a continuation-in-part of application Ser No. 076,312, filed Jun. 11, 1993, now U.S. Pat. No. 5,428,070.

BACKGROUND

The long term benefit of coronary balloon angioplasty and atherectomy is limited by the considerably high occurrence of symptomatic restenosis (40–50%) 3 to 6 months following the procedure (Holmes et al. Am. J. Cardiol. (1984) 53:77C–81C). Restenosis is in part due to myointimal hyperplasia, a process that narrows the vessel lumen and which is characterized by vascular smooth muscle cell migration and proliferation (Forrester et al. J. Am. Coll. Cardiiol. (1991) 17:758–769). Medical therapies to prevent restenosis have been uniformly unsuccessful. Intravascular stents have been successfully used to achieve optimal lumen gain, and to prevent significant remodeling. However, intimal thickening still plays a significant role in stent restenosis.

The vascular architecture is maintained or remodeled in response to the changes in the balance of paracrine factors. One of the substances that participates in vascular homeostasis is endothelium derived nitric oxide (NO). NO is synthesized from the amino acid L-arginine by NO synthase. NO relaxes vascular smooth muscle and inhibits its proliferation. In addition, NO inhibits the interaction of circulating blood elements with the vessel wall. NO activity is reduced in hypercholesterolemia and after vascular injury. We have shown that administration of the NO precursor (L-arginine) has been shown to restore vascular NO activity in animals and in humans with endothelial vasodilator dysfunction due to hypercholesterolemia, atherosclerosis, or restenosis. Chronic enhancement of NO activity (by oral administration of L-arginine) is associated with a significant reduction in intimal thickening due to hypercholesterolemia and/or vascular injury. The observations associated with the oral administration are limited to systemic action. Cooke, et al, J Clin Invest 1992; 90:1168–72; McNamara, et al, Biochem Biophys Res Comm 1993; 193:291–6; Taguchi, et al, Life Sciences 1993; 53:PL387–92; Tarry and Makhoul, et al, Arterioscler Thromb 1994; 14:938–43; Hamon, et al, Circulation 1994; 90:1357–62; Wang, et al, J Am Coll Cardiol 1994; 23:452–8.

However, oral administration of L-arginine has potential systemic side-effects. These side-effects include increases in growth hormone and insulin release—this could, potentially, exacerbate hyperglycemia in patients with diabetes (which is a large segment of the patient population that requires balloon angioplasty for coronary or peripheral artery disease). In addition, there is evidence that in high doses (30 grams daily) oral L-arginine can increase the proliferation of tumor cells in human breast cancer. Accordingly, it would be beneficial to develop an approach which would allow one to enhance NO activity selectively in the vessel wall where this effect is needed without having systemic side-effects. We have developed an approach to diminish the incidence of restenosis resulting from angioplasty and atherectomy, using arginine to enhance NO activity in the vessel wall, while at the same time avoiding potential systemic side-effects.

BRIEF DESCRIPTION OF THE RELEVANT LITERATURE

Intravenous oral administration of L-arginine can enhance the release of endothelium-derived nitric oxide from vessels of animals or humans with hypercholesterolemia and/or atherosclerosis (1–8). Chronic oral administration of L-arginine also inhibits the development of atherosclerosis in hypercholesterolemic animals (9–10). Oral administration of L-arginine also inhibits restenosis following balloon injury (11–13) as does oral L-arginine combined with application of L-arginine to the external surface of the vessel using a pluronic gel (14). However, oral or intravenous administration of L-arginine has systemic side-effects. Oral or intravenous L-arginine is known to induce the release of growth hormone and insulin; this could potentially exacerbate hyperglycemia in patients with diabetes. Moreover, one study has indicated that high doses of oral arginine can increase the proliferation of tumor cells in human breast cancer.

We have shown that intravascular administration of a plasmid construct containing the gene encoding nitric oxide synthase can increase NO production locally in the vessel wall and will inhibit restenosis in the rat carotid (15). However, this approach required direct exposure of the vessel and surgical arteriotomy as well as prolonged installation of the solution containing the NOS gene. This approach would be impractical for preventing restenosis in coronary arteries. Others have shown that administration of drugs consisting of nitric oxide, or releasing nitric oxide, can inhibit restenosis after angioplasty. Chronic inhalation of nitric oxide inhibits restenosis following balloon-induced vascular injury of the rat carotid artery (16). Oral administration of NO donors (drugs which release nitric oxide) inhibits restenosis in rat and pig models of balloon angioplasty-induced vascular injury (17,18). However, oral or inhaled administration of nitric oxide or nitric oxide donors have systemic effects (hypotension, headache); and are susceptible to drug tolerance (lack of effect of drug after prolonged administration. There is even some evidence in animal models that NO donors may accelerate atherosclerosis, possibly by suppressing endogenous NO activity in the vessel wall (19, 20).

1. Girerd X. J., Hirsch A. T., Cooke J. P., Dzau V. J., Creager M. A. L-arginfine augments endothelium-dependent vasodilation in cholesterol-fed rabbits. Circ Res 1990;67:1301–1308.
2. Cooke J. P., Andon N. A., Girerd X. J., Hirsch A. T., Creager M. A.: Arginine restores cholinergic relaxation of hypercholesterolemic rabbit thoracic aorta. Circulation 1991;83:1057–62.
3. Rossitch E., Jr., Alexander E., III, Black P., Cooke J. P. L-arginine normalizes endothelial function in cerebral vessels from hypercholesterolemic rabbits. J Clin Invest 1991;87:1295–1299.
4. Drexler H., Zeiher A. M., Meinzer K., Just H. Correction of endothelial dysfunction in coronary microcirculation of hypercholesterolemic patients by L-arginine. Lancet 1991;338:1546–1550.
5. Creager M. A., Gallagher S. J., Girerd X. J., et al. L-arginine improves endothelium-dependent vasodilation in hypercholesterolemic humans. J Clin Invest 1992;90:1248–53.
6. Kuo L, Davis M. J., Cannon M. S., Chilian W. M. Pathophysiological consequences of atherosclerosis extend into the coronary microcirculation. Restoration of endothelium-dependent responses by L-arginine. Circ Res 1992;70(3):465–76.
7. Tsao P. S., McEvoy L. M., Drexler H., Butcher E. C., Cooke J. P. Enhanced endothelial adhesiveness in hypercholesterolemia is attenuated by L-arginine. Circulation 1994;89:2176–82.
8. Drexler H., Fischell T. A., Pinto F. J., Chenzbraun A., Botas J., Cooke J. P., Alderman E. L. Effect of L-arginine on coronary endothelial function in cardiac transplant recipients: Relation to vessel wall morphology. Circulation 1994;89:1615–1623.
9. Cooke J. P., Singer A. H., Tsao P. S., Zera P., Rowan R. A., Billingham M. E. Anti-atherogenic effects of L-arginine in the hypercholesterolemic rabbit. J Clin Invest 1992;90:1168–72.
10. Wang B., Singer A., Tsao P., Drexler H., Kosek J., Cooke J. P.: Dietary arginine prevents
atherogenesis in the coronary artery of the hypercholesterolemic rabbit. J Am Coll Cardiol 1994;23:452–58.
11. McNamara D. B., Bedi B., Aurora H., Tena L., Ignarro L. J., Kadowitz P. J., Akers D. L. L-arginine inhibits balloon catheter-induced intimal hyperplasia. Biochem Biophys Res Comm 1993,193(1):291–6.
12. Tarry W. C., Makhoul R. G. L-arginine improves endothelium-dependent vasorelaxation and reduces intimal hyperplasia after balloon angioplasty. Arterioscler Thromb 1994;14(6):938–43.
13. Hamon M., Vallet B., Bauters C. H., Wernert N., McFadden E. F., Lablanche J. M., Dupuis D., Bertrand M. E. Long-term oral administration of L-arginine reduces intimal thickening and enhances neoendothelium-dependent acetylcholine-induced relaxation after arterial injury. Circulation 1994;90:1357–62.
14. Taguchi J., Abe J., Okazaki H., Takuwa Y., Kurokawa K. L-arginine inhibits neointimal formation following balloon injury. 1993;53(23):PL387–92.
15. von der Leyen H., Gibbons G. H., Morishita R., Lewis N. P., Zhang L., Nakajima M., Kaneda Y., Cooke J. P., Dzau V. J.: Gene therapy inhibiting neointimal vascular lesion: In vivo transfer of endothelial cell nitric oxide synthase gene. Proc Natl Acad Sci USA 1995;92:1137–41.
16. Lee J. S., Adrie C., Jacob H. J., Roberts J. D., Jr., Zapol W. M., Bloch K. D. Chronic inhalation of nitric oxide inhibits neointimal formation after balloon-induced arterial injury. Circ Res 1996;78(2):337–42.
17. Seki J., Nishio M., Kato Y., Motoyama Y., Yoshida K. FK409, a new nitric oxide donor, suppresses smooth muscle proliferation in the rat model of balloon angioplasty. Arterosclerosis 1995;117(1):97–106.
18. Groves P. H., Banning A. P., Penny W. J., Newby A. C., Cheadle H. A., Lewis M. J. The effects of exogenous nitric oxide on smooth muscle cell proliferation following porcine carotid angioplasty. Cardio Res 1995:30(1):87–96.
19. Munzel T., Syegh H., Freeman B. A., Tarpey M. M., Harrison D. G. Evidence for enhanced vascular superoxide anion production in nitrate tolerance. A novel mechanism underlying tolerance and cross-tolerance. J. of Clinical Investigation, 1995; (1):187–94
20. Bult H., Buyssens N., DeMeyer G. R. Y., Jordaens F. H., Herman A. G. Effects of chronic treatment with a source of exogenous nitric oxide on the release of endothelium-derived relaxing factor by aortae from normal and hypercholesterolemic rabbits. Elsevier Science Publishers B.V. (Biiomedical Division) Nitric oxide from L-arginine: a bioregulatory system. Moncada S., Higgs, editors. 1990; Chapter 13, pp. 101–106.

SUMMARY OF THE INVENTION

Methods and devices are provided for inhibiting the pathology associated with vascular injury, particularly during angioplasty and atherectomy. An NO precursor, particularly L-arginine, is intramurally introduced into the walls of the injured vessel in proximity to the injury in an amount to inhibit the pathology, e.g. restenosis, associated with the vascular injury. Various conventional delivery devices may be used for intramural delivery of the NO precursor, which are loaded with the NO precursor.

DESCRIPTION OF THE SPECIFIC EMBODIMENTS

Methods and devices are provided for the treatment of pathologies associated with vascular injury, particularly in relation to angioplasty and atherectomy. Of particular interest is the injury referred to as restenosis, which results from the migration and proliferation of vascular smooth muscle cells into the intima of the vessel as well as accretions associated with the atherosclerosis.

The method provides introducing into the vessel walls at the site of injury an NO precursor, which results in the enhancement of NO production in the cells at the site of injury. Various delivery systems may be employed which result in the NO forming agent infusing into the vessel wall, and being available to the cells for NO production. Devices which may be employed include drug delivery balloons, e.g. porous, sonophoretic, and iontophoretic balloons, as exemplified by the devices depicted in WO92/11895, WO95/05866 and WO96/08286, as well as such commercial devices as Dispatch® (Scimed). See also Santoian et al., *Cath. Cardiov. Diag.* (1993) 30:348–354; Muller et al., *J. Am. Coll. Cardiol.* (1992) 20:460–466; and Ortiz et al., *Circulation* (1994) 89:1518–1522. The NO precursor agent is introduced in a delivery balloon for transport by a catheter to the site of injury. The balloon may then be expanded under pressure driving the agent from the balloon into the surrounding vessel wall. The amount of agent which is employed may vary depending upon the nature of the agent, the region to be treated, and the loss of the agent from the region. The infusion of the agent is maintained for sufficient time to ensure that the cells and extracellular matrix in the injury region are exposed to the agent, so as to enhance the production of NO by these cells.

The agent may have a single active ingredient or be a combination of active ingredients. Of particular interest are the amino acids, L-arginine and L-lysine, individually or in combination, as a mixture or as an oligopeptide, or a biologically equivalent compound, such as low molecular weight oligopeptides, having from about 2–10, usually 2–6 amino acids, or acetylated amino acids and oligopeptides, etc.

Other agents may be employed to enhance the amount of nitric oxide, either directly by enhancing production of nitric oxide, e.g. by enhancing absorption, and/or to enhance the activity of NO synthase, or to protect NO from degradation. Generally, the dose range will be about 0.2 to 0.05 the amount that would be administered orally on a daily dosage. These compounds include vitamin $B_6$ (5–25 mg), folate (0.04–1 mg), vitamin $B_{12}$ (0.05–0.1 mg), cysteine or N-acetyl cysteine (20–100 mg), vitamin C (25–200 mg), coenzyme Q (2.5–9 mg), glutathione (5–25 mg), vitamin E (20–100 I.U.), β-carotene (1–2500 I.U.) or other physiologically acceptable antioxidants, such as tocopherols, phenolic compounds, thiols, and ubiquinones. These additional additives will generally be present in relatively small amount in the formulation, generally being present in less than about 10 weight percent, more usually less than about 5 weight percent, frequently less than about 1 percent, and in at least about 0.01 weight percent of the nitric oxide precursor.

A physiologically acceptable medium will be employed, normally an aqueous medium, which may be deionized water, saline, phosphate buffered saline, etc. The amount of the active NO precursor agent will vary depending upon the particular agent employed, the other additives present, etc. Generally, as exemplified by L-arginine, at least about 50 mg will be present, and not more than about 5 g, usually at least about 100 mg, and not more than about 2 g, frequently at least about 500 mg. The concentration may be varied widely, generally ranging from about 20–500, more usually from about 50–250 g/l.

The time for the treatment will usually be at least about 2 minutes, and not more than about 0.5 hour, generally ranging from about 5–15 minutes. The rate of introduction will generally range from about 0.05–5 ml/min, depending upon all of the other factors.

The subject methodology is employed with hosts who have suffered vascular injury, as caused by angioplasty and atherectomies. The time for the administration of the NO precursor agent may be varied widely, providing a single administration or multiple administrations over a relatively short time period in relation to the time of injury. Generally, treatment may be before, concurrently or after the injury, usually within 2 weeks of the injury, if before, and not more than about 8 weeks, usually not more than about 6 weeks, preferably in the range of 0–6 weeks (where 0 intends concurrrently or shortly after the prior procedure, within 6 hours).

For the most part, the patients will be suffering from various conditions associated with narrowed vessels, particularly hypercholesterolemia, diabetes, tobacco use and hypertension. Thus, one will normally be dealing with vessels which are narrowed to varying degrees as a result of the accumulation of plaque at the vessel wall.

It is found that with one treatment of the NO precursor agent at or about the time of the injury, before or shortly thereafter, one can observe enhanced vascular NO production and reduced intimal thickening, so as to substantially reduce the potential for restenosis.

Figure 8:
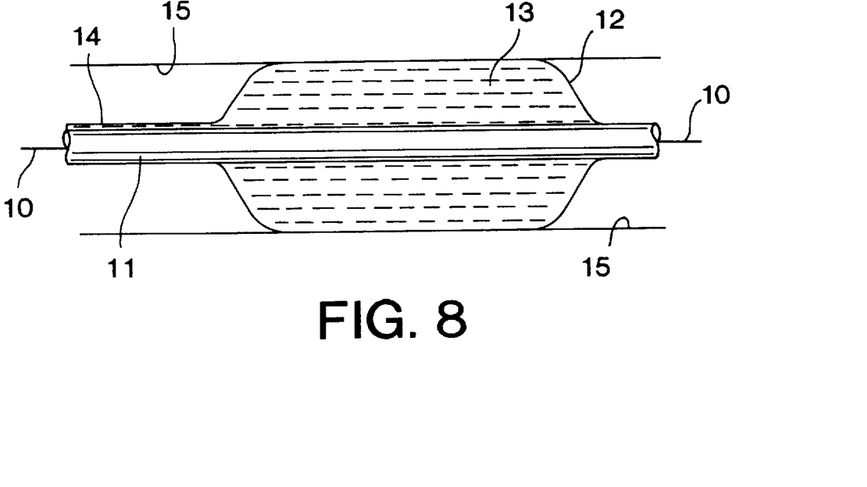
FIG. 8 is a fragmentary view, partially in section, of a drug delivery apparatus for use in the subject invention positioned in a blood vessel with the dilatation balloon in its inflated state and containing a solution of an NO precursor.

As indicated, various delivery devices may be employed for the delivery of the active agent. FIG. 8 illustrates the drug delivery apparatus with the balloon 12 in its inflated state and within an arterial vessel in which the vessel walls are indicated by the reference numeral 15. During percutaneous transluminal coronary angioplasty ("PCTA") procedures, the guide wire 10 is first inserted into the selected artery to a point past the stenotic lesion. The dilatation catheter including the catheter body 11 and the balloon 12 is then advanced along the guide wire 10 to the desired position in the arterial system in which the balloon portion 12 traverses or crosses the stenotic lesion. The balloon 12 is then inflated by introducing the NO precursor solution through the balloon lumen 14 into the interior chamber 13 of the balloon 12. During inflation, the outer surfaces of the balloon 12 press outwardly against the inner surfaces of the vessel wall 15 to expand or dilate the vessel in the area of the stenotic lesion, thus performing the angioplasty portion of the method as well as the intramural introduction of the NO precursor into the vessel wall.

The porous balloon may be made from any of the conventional materials used for this purpose. These include cellulose acetate, polyvinyl chloride, polysulfone, polyacrylonitrile, polyurethanes, natural and synthetic elastomers, polyolefins, polyesters, fluoropolymers, etc. Usually the film thickness will be in the range of about 10 Å to 1μ, with a nominal pore size of about 0.05 to 1μ. Alternatively, a local drug delivery system may be employed where the agent is delivered to the vessel wall by channels that are on the exterior surface of the balloon. The balloon is placed into the diseased vessel segment as described above. The balloon is then inflated in the usual manner (using saline, usually containing a contrast agent), placing the channels (on the surface of the balloon) in contact with the vessel wall. The NO precursor solution is then infused under pressure into the channels. Perforations in the channels allow the solution to exit and jet into the vessel wall under pressure to enhance intramural delivery.

Alternatively, a local drug delivery system may be employed where the agent is delivered to the vessel wall by channels that are on the exterior surface of the balloon. The balloon is placed into the diseased vessel segment as described above. The balloon is then inflated in the usual manner (using saline, usually containing a contrast agent), placing the channels (on the surface of the balloon) in contact with the vessel wall. The NO precursor solution is then infused under pressure into the channels. Perforations in the channels allow the solution to exit and jet into the vessel wall under pressure to enhance intramural delivery.

Figure 9:
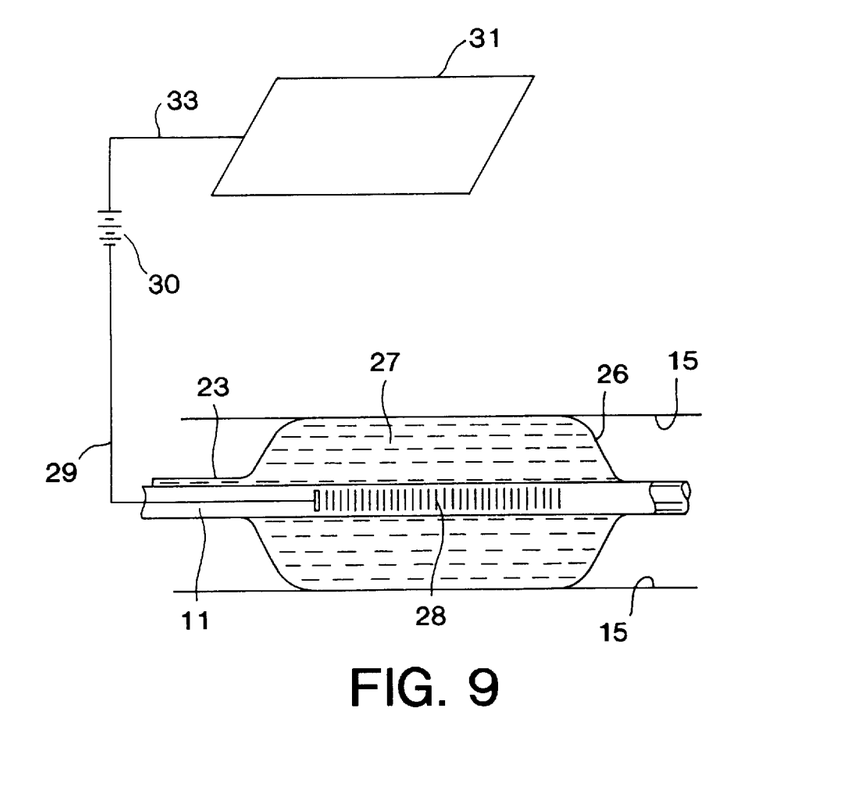
FIG. 9 is a fragmentary view, partially in section, of the NO precursor drug delivery apparatus positioned in a blood vessel and embodying iontophoresis means to transport the drug across the balloon surface.

Alternatively, an iontophoretic approach may be used. FIG. 9 illustrates a structure utilizing iontophoresis to assist in driving the active NO precursor across the balloon wall 26 and into contact with the vessel walls 15. One electrode 28, the catheter electrode, is located on or within the catheter body 11, while the other electrode 31, the body surface electrode, is located on the body surface or within the body of the patient. An electrical current for the iontophoretic process is produced between the electrodes 28 and 31 by an external power source 30 through the electrical leads 29 and 33, respectively. Direct current may be used, although other wave forms are also utilized (e. g., a series of rectangular waves producing a frequency of 100 Hz or greater).

During operation of the iontophoretic device, the balloon 26 is first positioned across the stenotic lesion. The balloon interior 27 is then inflated with the drug in the lumen 23. As the balloon expands, it causes the artery to dilate. This is followed by activating the power supply 30, thereby creating a current between the electrode 28 and the electrode 31 which passes through the balloon wall 26. This current drives or drags the NO precursor within the chamber 27 across the wall and into contact with the surrounding vessel wall 15 and vascular tissue.

The following examples are offered by illustration, and not by way of limitation.

EXPERIMENTAL

Methods

Animals 27 male New Zealand white rabbits (NZW) weighing 3.8±1.5 kg, were entered into the study after one week period of acclimation in the housing facilities of the Stanford Department of Comparative Medicine. All animals were inspected prior to the study by a veterinarian, and monitored daily by technicians and investigators. The experimental protocols were approved by the Administrative Panel on Laboratory Animal Care of Stanford University and were performed in accordance with the recommendations of the American Association for the Accreditation of Laboratory Animal Care.

Animals were then fed a high cholesterol diet (1%, Dyets, Bethlehem, Pa.) for five weeks. Two protocols (acute and chronic study) were carried out as follows: (FIGS. 1A & B) Acute Study (n=13; protocol see FIG. 1A). This study was performed to determine if intramural administration of the NO precursor L-arginine could enhance local NO synthesis.

Anesthesia and Surgical Preparation

Six days after initiating the high cholesterol diet, the rabbits were anesthetized using a mixture of ketamine (5 mg/kg) and rompun (35 mg/kg). The right carotid artery was exposed, carefully incised and a tygon sheath (5 French in diameter) was inserted under fluoroscopic control into the descending aorta. An angioplasty balloon (ACS, balloon diameter 3 mm) was advanced into either iliac artery and inflated distal to the deep femoral artery at 8 ATM for 6 times with 30 second increments between each inflation. Subsequently, the same procedure was repeated in the contralateral iliac artery. After four additional weeks of diet, the animals were anesthetized and the left carotid artery cannulated for catheterization—and local drug delivery.

Local Drug Delivery

A local drug delivery balloon (3 mm, Dispatch®, Scimed) was advanced to the left or right iliac artery and placed at the same position as the previous balloon injury. The proximal end of the delivery catheter was placed at the internal iliac branch under fluoroscopic control for landmark reference. The balloon was inflated to six atmospheres and L-arginine (800 mg/5 ml), or saline was infused for 15 minutes at a rate of 0.2 ml/minute. Subsequently, this procedure was repeated in the contralateral iliac artery. The iliac artery to receive arginine treatment was randomly determined. An intravenous bolus injection of Kefzol® was given for prevention of infections.

Identification of Endothelium-Dependent Vasomotion and Quantitative Angiography

After local administration of arginine or saline, a control angiogram was obtained. Subsequently, two infusions containing acetylcholine ($10^{-5}$, $10^{-6}$M) were administered at a rate of 0.8 ml/minute for 3 minutes through a Swan Ganz catheter (4 French in diameter), placed above the iliac bifurcation. Immediately following each infusion, an angiogram of the iliac arteries was performed. All angiograms were measured blindly by two investigators with an electronic caliper system. The diameter was measured at three predetermined sites along the area of drug delivery at baseline and after each dose of acetylcholine before and after the local drug delivery. The vessel diameter was also measured at a reference site distal to the infusion segment to verify downstream effects of locally delivered L-arginine. The percent variation in diameter compared to baseline was calculated for each dose and expressed in mean±SEM.

Harvesting of Tissue 30 to 60 minutes following the local delivery of L-arginine, animals were sacrificed and the iliac arteries carefully freed from adjacent tissue. Care was taken to harvest the exact portion of the artery where the local delivery was carried out by matching the anatomy with the respective fluoroscopic picture. To verify the amount of cell damage induced by the local drug delivery balloon, electron microscopy of the delivered segment was performed in three rabbits.

Measurements of Nitrogen Oxide

The harvested iliac artery rings were placed in cold physiological solution. The vessel was opened longitudinally and incubated in 2 ml of Hanks buffered saline (HBSS) medium (Irvine Scientific) containing calcium ionophore (1 $\mu$mol/L, A23187, Sigma, St. Louis, Mo.) and L-arginine (100 $\mu$l/L, Sigma, St. Louis, Mo.) at 37° C.

At selected time points (0, 30, 60, 120 minutes), samples of the medium were collected for measurements of nitrogen oxide (NOx) and replaced with 2 ml of fresh media. After incubation, the segment was weighed and NOx was measured with a commercially available chemiluminescence apparatus (model 2108, Dasibi). 100 $\mu$l of the samples were injected into a reduction chamber containing boiling acidic vanadium (III). In the reduction chamber, $NO_2$— and $NO_3$— are reduced to NO, which is then quantified by the chemiluminescence detector after reaction with ozone. Signals from the detector were analyzed by a computerized integrator and recorded as areas under the curve. Standard curves for $NO_2/NO_3$ were linear over the range of 50 pmol to 10 nmol.

Chronic Study (n=14; protocol see FIG. 1B)

This study was performed to determine if a single intramural administration of L-arginine could induce a persistent augmentation of NO activity and inhibit myointimal hyperphasia and/or macrophage accumulation. One week after initiation of the diet, a balloon injury of the iliac arteries was performed under anesthesia. Immediately thereafter, L-arginine was administered into the wall of the right or the left iliac artery by the local delivery system. Saline was administered using the same catheter system to the contralateral iliac artery. The dose of L-arginine and the infusion rate was identical to that used in the acute study. One, two, or four weeks (n=4, 4, and 6 respectively) after balloon injury and local drug delivery, endothelium-dependent vasomotion was assessed angiographically and/or vessels were harvested for histomorphometric measurements immunohistochemistry, or chemiluminescence.

Morphometric Analysis (Intima/Media Ratio)

The harvested vessels were fixed in 10% buffered formalin and then embedded in paraffin. The embedded vessels were sectioned into thin slices and stained with hematoxylin and eosin for light microscopy and histomorphometry. Measurements of intimal and medial cross-sectional area were made by experienced observers blinded to the treatment group. Histologic cross-sections were scanned with one magnification and digitized, using the Image Analysist. The following borders were highlighted with a trackball: external elastic lamina, internal elastic lamina, lumen/intima border. Cross sectional areas of the respective vessel wall layers were then calculated and an intima/media ratio calculated. The media was defined as the area between the external and the internal elastic lamina, the intima was defined as the vessel layer between the internal elastic lamina and the intimal/luminal border.

Immunohistochemistry

Immunohistochemical analysis was performed on tissue fixed in formaldehyde and embedded in paraffin as described above. Antibodies against rabbit macrophage (RAM 11, Dako Corp., Carpenteria, Calif.) was used to identify macrophages. Sections were incubated with the primary antibody for one hour at room temperature, anti-rabbit IgG (biotin conjugate) for 30 minutes and avidin peroxidase for 20 minutes. Peroxidase was then visualized with CHROMOGEN (Zymed Laboratories, Inc., South San Francisco, Calif.). Three respective cross-sections were immunostained for each vessel segment treated with either L-arginine or saline. Macrophage staining was assessed by two experienced observers using a light microscope. Areas of the vessel defined as media and intima and the percent of the vessel stained for macrophage was determined.

Nitrogen/Oxide Measurements

In four rabbits, tissue was harvested one week following the local delivery of L-arginine for measurements of NOx levels. Chemiluminescence measurements were made as described above.

Data Analysis

Data are expressed as mean±SEM. The difference in vasoreactivity to acetylcholine was expressed as percentage variation in diameter compared to baseline. The mean change of all arteries in each treatment group (L-arginine or saline) was used for comparison. An unpaired t-test was performed to compare values between the two-treatment groups for each dose of acetylcholine before and following either L-arginine or saline. Additionally, a two-factor analysis of variance was performed to verify the difference within the treatment group and between the groups. Significantly different changes were assumed at a p-value of $\leq 0.05$. Differences between NOx levels were also identified using Student's t-test with Bonferroni correction for multiple comparisons.

Results

Figure 1A:
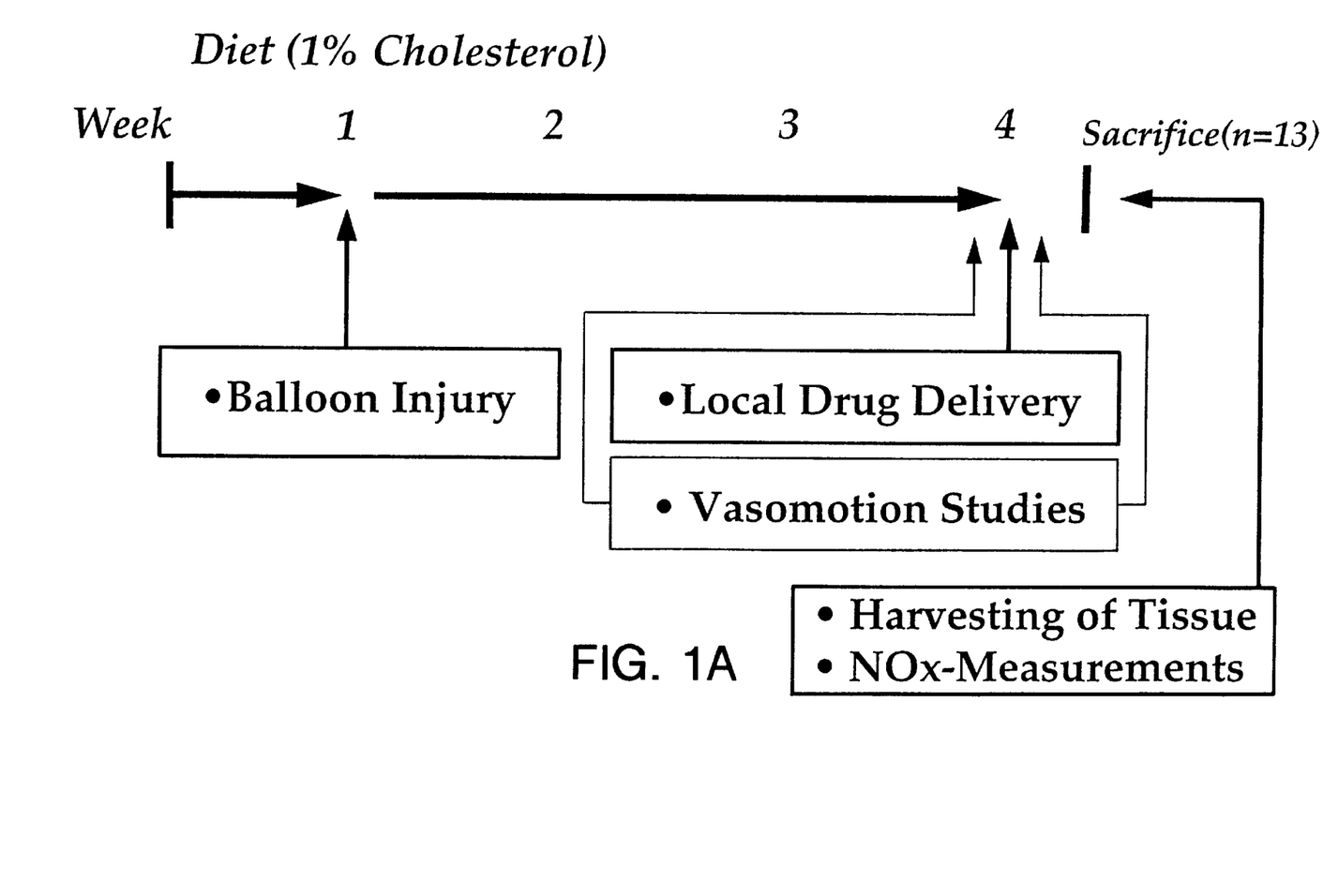
FIGS. 1A and 1B are schematic diagrams explaining the treatment and experimental protocol of the acute study (FIG. 1A) and the chronic study (FIG. 1B).
Figure 1B:
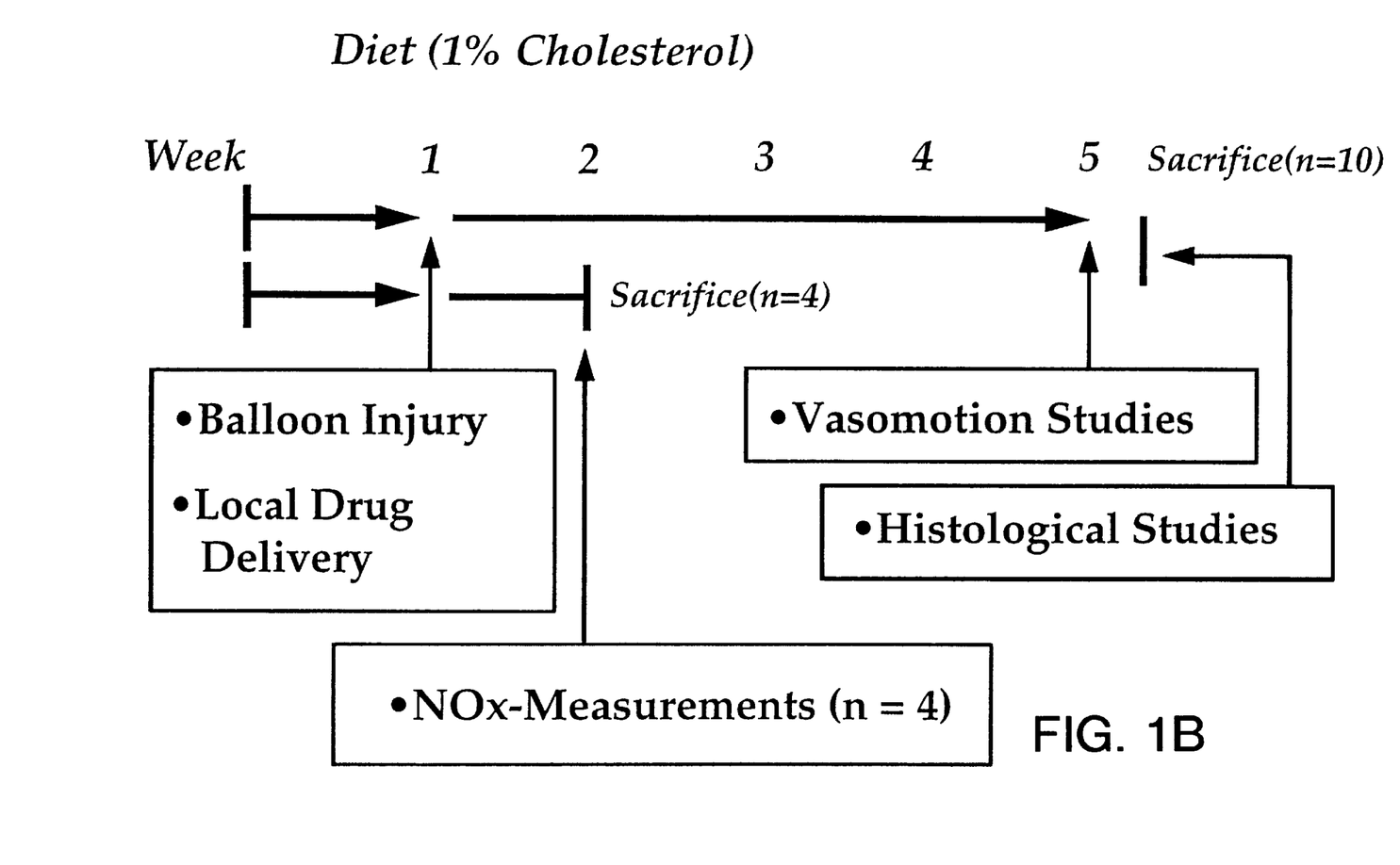

Acute Study (FIG. 1A)

Vasoreactivity

Figure 2A:
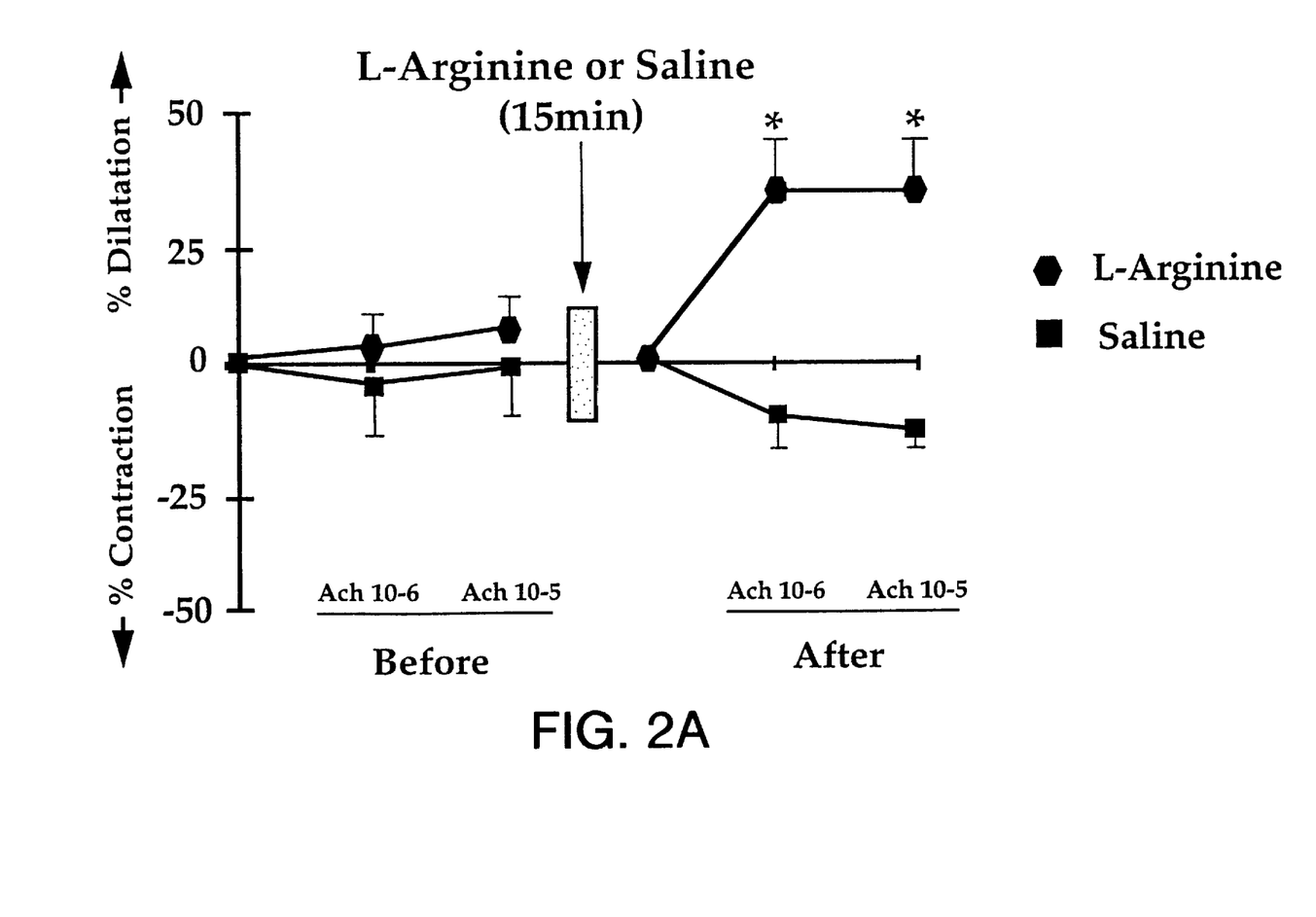
FIG. 2A shows the endothelium-dependent vasomotion before and following the local delivery of L-arginine. The Y axis shows % constriction and dilatation, the X axis the course of the experiment. Before the L-arginine there was only a minor change in diameter in both iliac arteries. Following the local delivery of L-arginine, treated segments showed significant dilatation. The control segments are constricted. *=p<0.001.
Figure 2B:
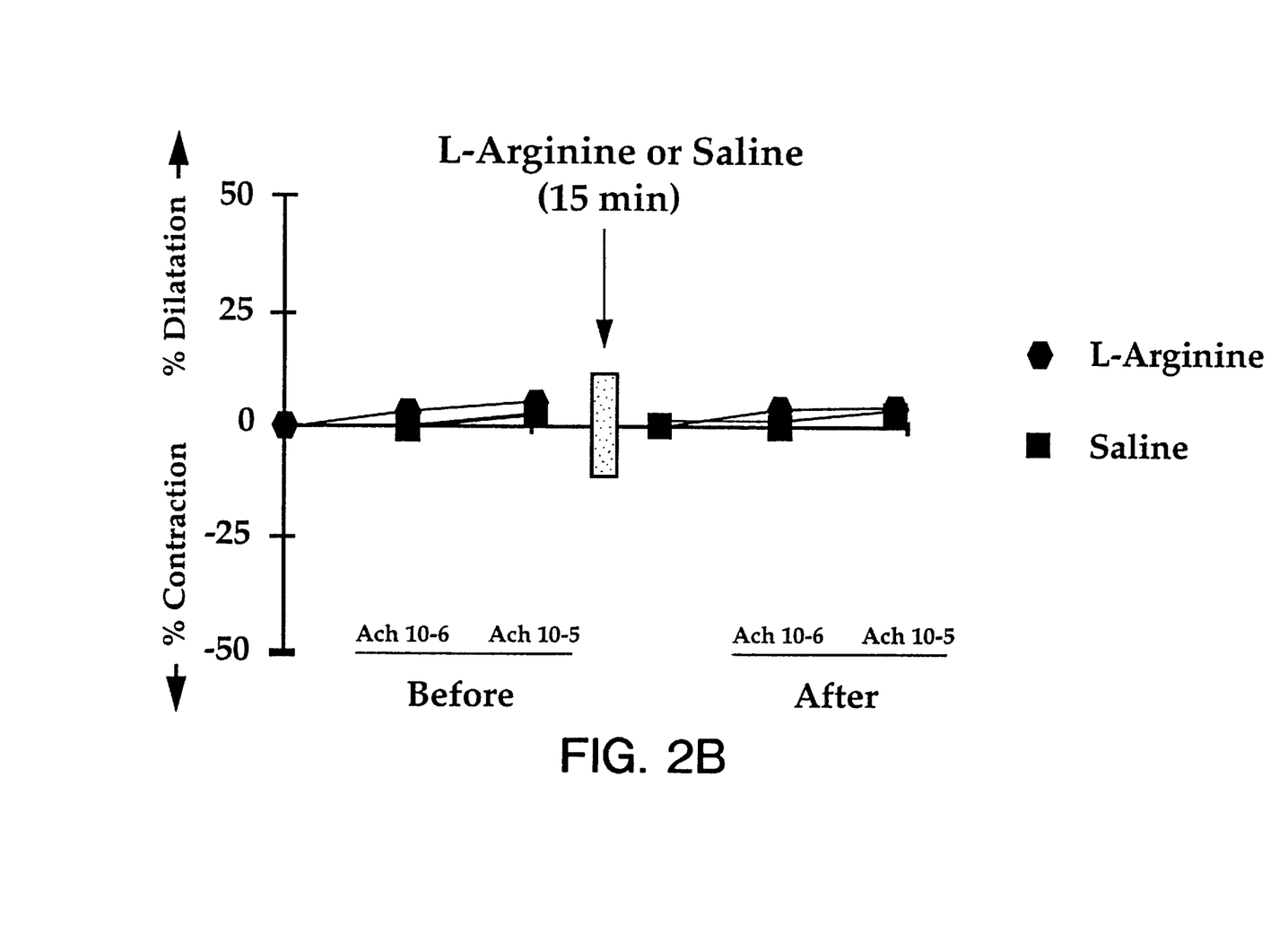
FIG. 2B is a graph showing that the vessel segments distal to the delivery site did show only minor changes in vessel diameter to acetylcholine and were not affected by the L-arginine delivery.
Figure 3A:
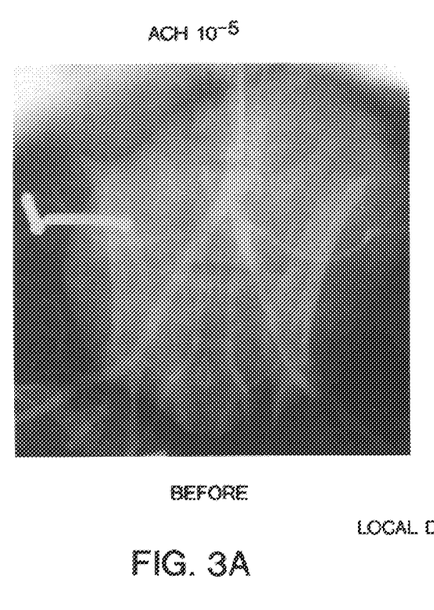
FIG. 3 is a representative aortogram in the hypercholesterolemic rabbit. Before Ach infusion (left panel, $10^{-5}$M), the vessel diameter of the iliac arteries are identical. Following the local drug delivery (right panel), the right iliac artery dilates to the same dose of Ach after receiving L-arginine.
Figure 3B:
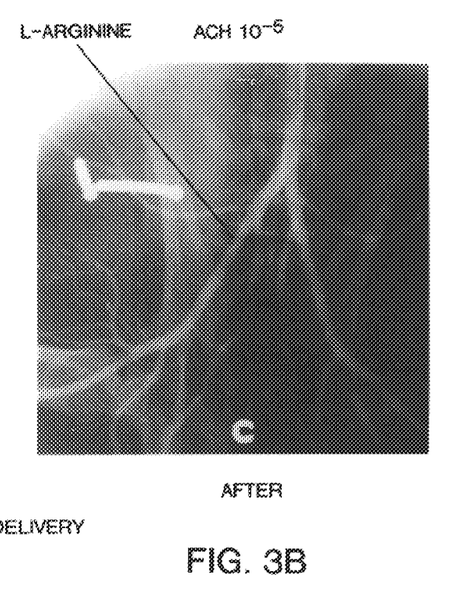

FIG. 2A shows the response of vessel segments to acetylcholine before and after the local delivery of L-arginine or saline. Baseline vessel diameters were identical before and after local drug delivery in both iliac arteries. There was little change in vessel diameter before local drug delivery. This probably reflects the fact that acetylcholine-induced endothelium-dependent vasodilation is attenuated in the endothelium that regenerate after vascular injury, particularly in the setting of hypercholesterolemia. After local delivery of L-arginine, endothelium-dependent vasodilation was restored. By contrast, after local delivery of the vehicle, no vasodilation was observed. The effect of L-arginine was localized to the segment which was exposed to intramural delivery. Almost no change in vessel diameter was seen at the site distal to the local delivery of L-arginine (FIG. 2B). Thus, using this method only local (rather than systemic) effects of L-arginine were observed.

Nitrogen Oxide Levels

NOx measurements were made in vessel segments harvested 30–60 minutes after local drug delivery. Vessel segments treated with arginine exhibited a significant increase in nitrogen oxide levels throughout the incubation periods of 30, 60 and 120 minutes.

Chronic Study (FIG. 1B)

Vasoreactivity

Vasomotion studies were performed two or four weeks after the local drug delivery. Iliac arteries treated with vehicle tended to vasoconstrict in response to acetylcholine whereas those treated with L-arginine tended to vasodilate although the observed differences did not reach statistical signance (Ach $10^{-1}$M; 2.2±1.3% vs −4.2±3.8%, L-arginine vs. vehicle. Ach $10^{-5}$; 7.2±1.0 vs. −4.0±7.5).

Intima Media Ratio

Figure 5:
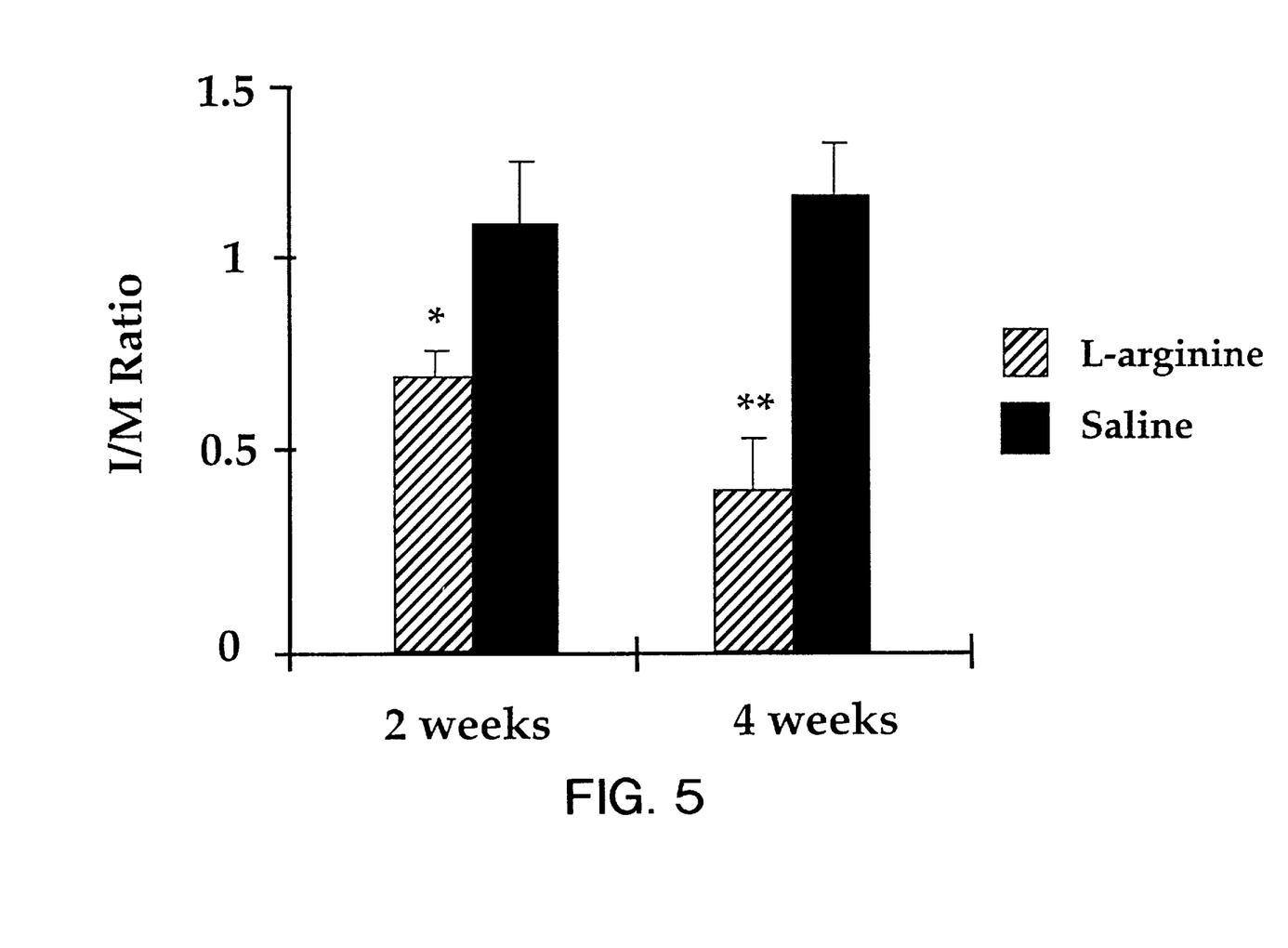
FIG. 5 is a bar graph of Intima/Media ratios at 2 and 4 weeks following local drug delivery. Intima/Media ratios were significantly lower in the L-arginine treated groups after 2 and 4 weeks in comparison to vehicle-treated vessels (*p<0.04, **p<0.01).
Figure 6A:
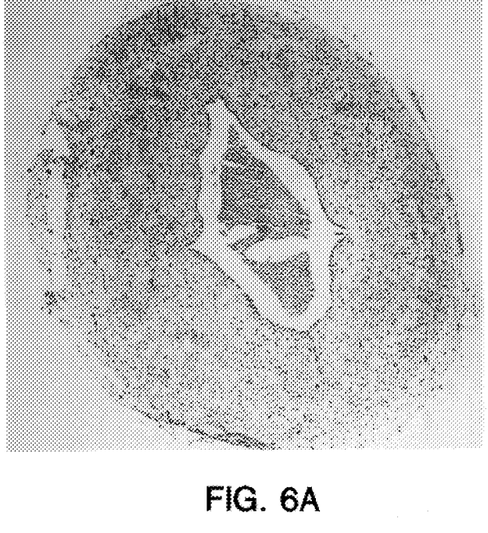
FIGS. 6A and 6B depict low power microphotographs of iliac arteries of hypercholesterolemic rabbits 4 weeks after balloon catheter injury and local drug delivery. Intimal thickening is markedly reduced in the vessel segment treated with L-arginine (6B) in a comparison to that treated with vehicle (6A).
Figure 6B:
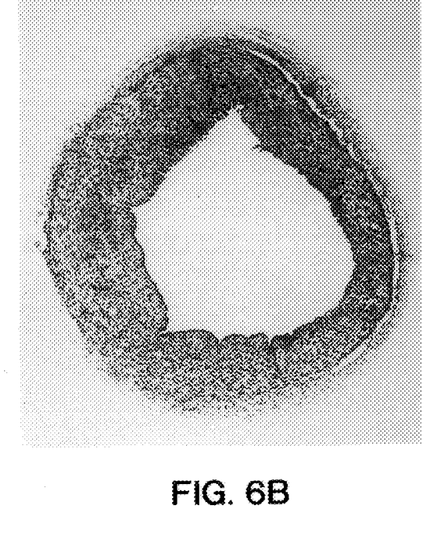

FIG. 5 shows the results obtained two and four weeks following local drug delivery. Administration of L-arginine significantly inhibited intimal lesion formation in comparison to vehicle control. This phenomenon was even more apparent four seeks following local drug delivery.

Immunohistochemistry

Figure 7:
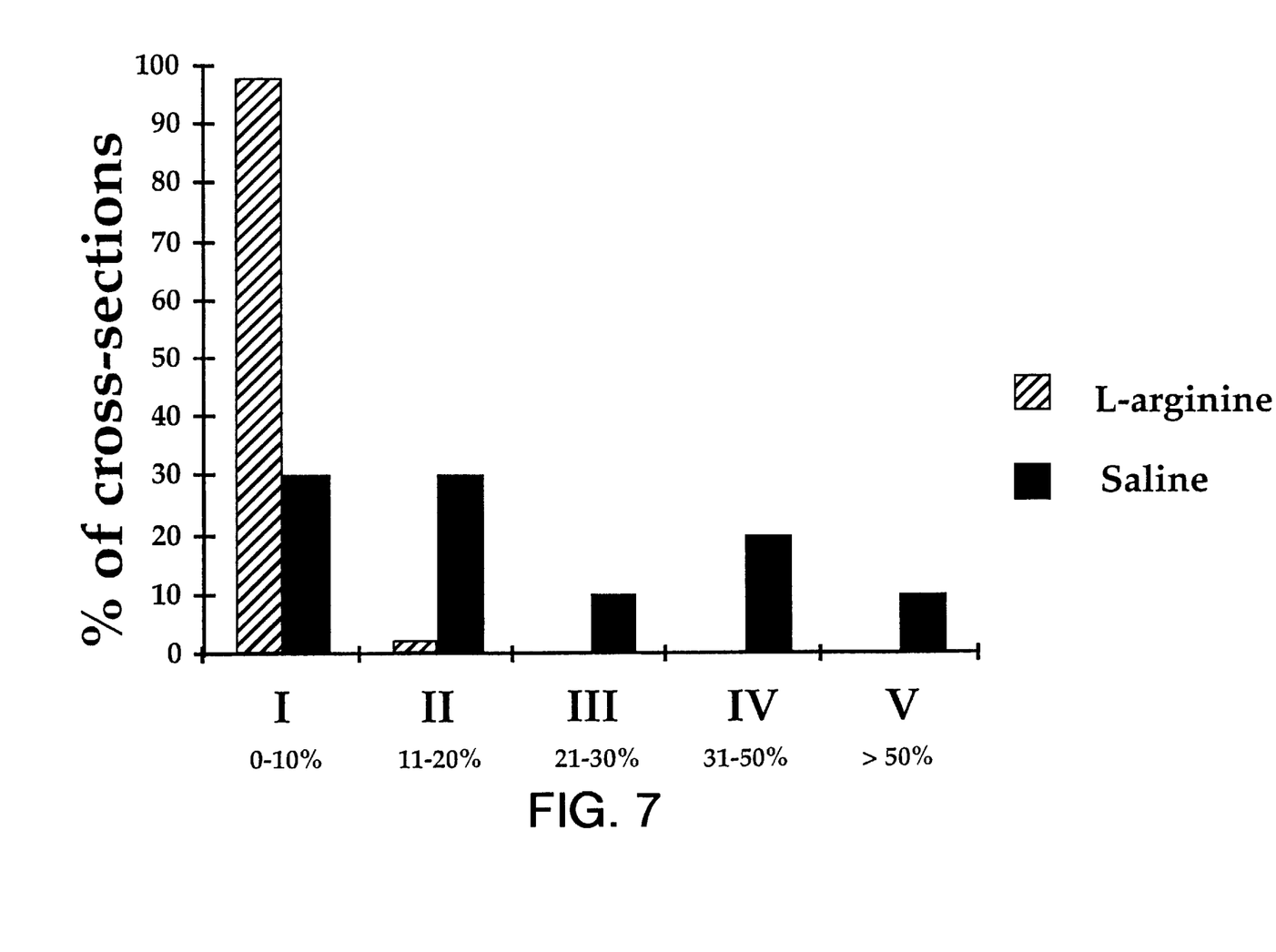
FIG. 7 are histograms illustrating the percentage of intimal lesion occupied by macrophages. In vessel segments treated with L-arginine (striped bars) macrophage accumulation did not exceed 20% of the intimal area. By contrast, in vehicle treated segments, macrophages occupied up to 70% of the intimal area in some cases.

FIG. 7 shows the percentage of the intimal lesion surface area which stained positively for macrophages. Only 0–10% of the intimal area was infiltrated by positively stained cells in the L-arginine treated segments, whereas in vessel segments treated with vehicle, the intimal area involved by macrophages was markedly higher, in some segments exceeding 50% of the intimal area.

Nitrogen Oxide Levels

Figure 4:
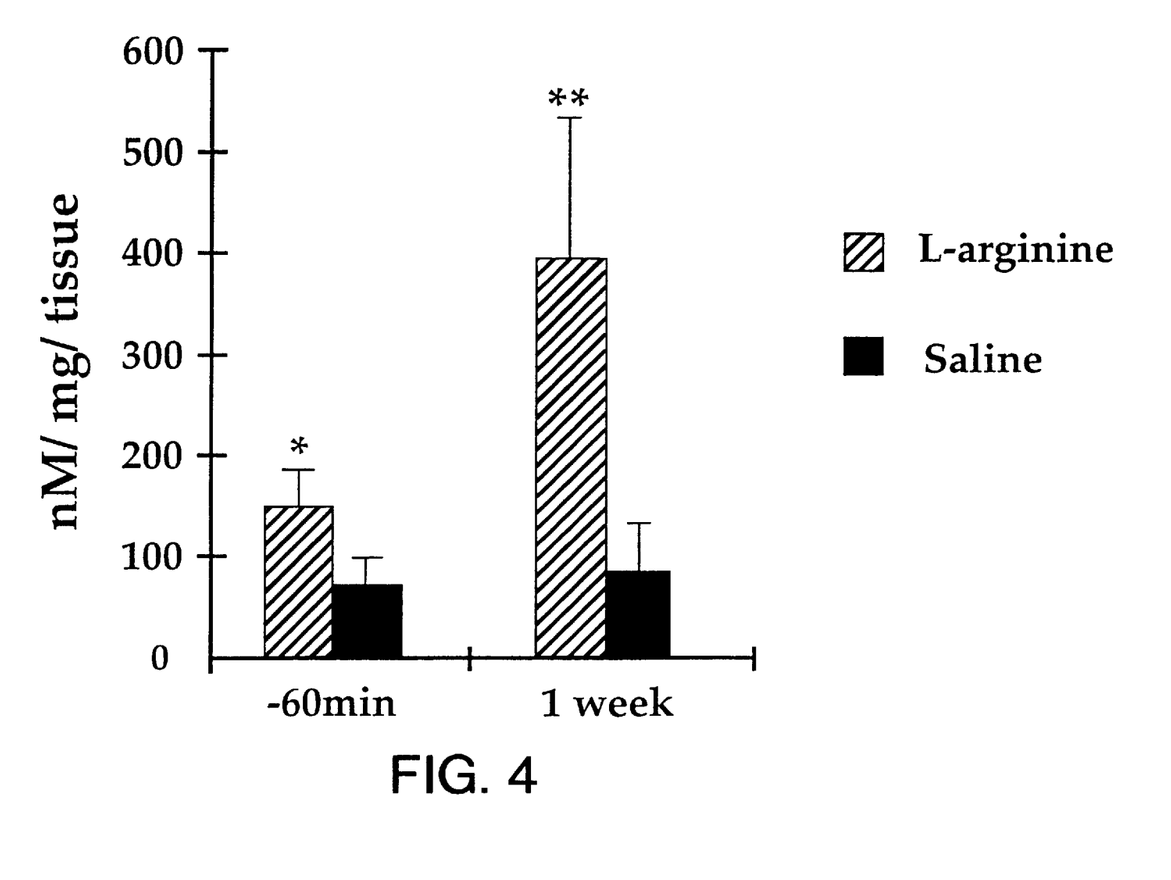
FIG. 4 is a graph showing maximum nitric oxide production 1 hr and 1 week following drug delivery. Vessels treated with L-arginine (striped bars) showed significantly higher production of nitric oxide compared to vessels treated with vehicle (dark bars) (*p<0.04, **p<0/01). Absolute values 1 week after the delivery were considerably higher compared to those obtained 1 hr after the delivery of L-arginine.

In vascular segments from four rabbits, NO was measured. NO production ex vivo was significantly higher one week following the delivery of L-arginine compared to segments exposed to vehicle. These levels were also higher compared to those achieved one hour following the delivery (FIG. 4).

It is obvious from the above results, that the subject methodology and devices provides an alternative treatment to substantially reduce the occurrence of restenosis after vascular injury. The methodology is simple, can be performed in conjunction with the procedure resulting in the vascular injury, and is found to be effective. Importantly, this approach avoids systemic side effects associated with oral or intravenous administration of L-arginine, while providing effective treatment. In this way, a procedure which has been commonly used can find expanded application as a result of the reduced incidents of restenosis.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method to perform angioplasty or atherectomy comprising introducing a balloon catheter into a vascular vessel proximal to a lesion site, inflating the balloon to expand the vessel proximal to said lesion site, deflating said balloon and removing said balloon catheter from said vascular vessel, the improvement which comprises:

introducing intramurally into the vascular vessel by means of said balloon catheter at least one of L-arginine or L-lysine, in an amount to increase the amount of nitric oxide formation of the cells proximal to said lesion site, prior to removal of said balloon catheter from said vascular vessel, whereby a reduced incidence of restenosis occurs.

2. A method according to claim 1, wherein said introducing is for at least two minutes and not more than 0.5 hr. and at a rate of from about 0.05–5 ml/min of an aqueous solution of a concentration in the range of about 20–500 g/l.

3. A method according to claim 1, wherein L-arginine is introduced.

4. A method according to claim 1, where L-lysine is introduced.

5. A method according to claim 1, wherein said at least one of L-arginine or L-lysine is introduced under pressure.

6. A method according to claim 1, wherein said at least one of L-arginine or L-lysine is delivered iontophoretically.

7. In a method to perform angioplasty or atherectomy comprising introducing a balloon catheter into a vascular vessel proximal to a lesion site, inflating the balloon to expand the vessel proximal to said lesion site, deflating said balloon and removing said balloon catheter from said vascular vessel, the improvement which comprises:

introducing intramurally into the vascular vessel by means of said balloon catheter at least one of L-arginine or L-lysine for at least 5 minutes and not more than 15 minutes and at a rate of from about 0.05–5 ml/min of an aqueous solution of a concentration in the range of about 20–500 g/l, in an amount to increase the amount of nitric oxide formation of the cells proximal to said lesion site, prior to removal of said balloon catheter from said vascular vessel, whereby a reduced incidence of restenosis occurs.

* * * * *

UNITED STATES PATENT AND TRADEMARK OFFICE
CERTIFICATE OF CORRECTION

PATENT NO. : 5,852,058
DATED : December 22, 1998
INVENTOR(S) : J.P. Cooke, S. Schwarzacher, T.T. Lim and A.C. Yeung It is certified that error appears in the above-identified patent and that said Letters Patent is hereby corrected as shown below:

In column 1, before line 15, insert the following:
--GOVERNMENT LICENSE RIGHTS
This invention was made with Government support under contract HL02668 awarded by the National Institutes of Health. The Government has certain rights in this invention.--.

In column 11, line 14, change "proximal" to --proximate--;
In line 20, change "proximal" to --proximate--.

In column 12, line 12, change "proximal" to --proximate--;
In line 13, change "proximal" to --proximate--;
In line 23, change "proximal" to --proximate--.

Signed and Sealed this

Twenty-fifth Day of July, 2000

Q. TODD DICKINSON

*Attest:*

*Attesting Officer*              *Director of Patents and Trademarks*